United States Patent [19]
Wigness et al.

[11] Patent Number: 5,290,263
[45] Date of Patent: Mar. 1, 1994

[54] BIDIRECTIONAL CHECK VALVE CATHETER

[75] Inventors: Bruce D. Wigness; Frank D. Dorman, both of Minneapolis, Minn.

[73] Assignee: Regents of the University of Minnesota, Minneapolis, Minn.

[21] Appl. No.: 919,984

[22] Filed: Jul. 27, 1992

Related U.S. Application Data

[63] Continuation of Ser. No. 616,737, Nov. 21, 1990, abandoned, which is a continuation of Ser. No. 305,971, Feb. 2, 1989, abandoned.

[51] Int. Cl.$^5$ ............................................. A61M 5/00
[52] U.S. Cl. ...................................... 604/247; 604/93; 604/256
[58] Field of Search .............. 604/93, 102, 246, 247, 604/256, 280; 600/16-18

[56] References Cited

U.S. PATENT DOCUMENTS

| | | | |
|---|---|---|---|
| 2,747,608 | 5/1956 | Grove. | |
| 3,592,184 | 7/1971 | Watkins | 600/18 |
| 3,995,617 | 12/1976 | Watkins et al. | 604/247 |
| 4,014,317 | 3/1977 | Bruno | 604/247 |
| 4,246,932 | 1/1981 | Raines. | |
| 4,327,722 | 5/1982 | Groshong et al. | |
| 4,431,426 | 2/1984 | Groshong et al. | 604/280 |
| 4,529,399 | 7/1985 | Groshong et al. | |
| 4,549,879 | 10/1985 | Groshong et al. | |
| 4,657,536 | 4/1987 | Dorman | 604/247 |
| 4,671,796 | 6/1987 | Groshong et al. | |
| 4,701,166 | 10/1987 | Groshong | 604/247 |
| 4,705,501 | 11/1987 | Wigness et al. | 604/43 |
| 4,725,266 | 2/1988 | Siposs. | |
| 4,753,640 | 6/1988 | Nichols et al. | 604/247 |
| 4,846,806 | 7/1989 | Wigness et al. | 604/256 |
| 4,857,054 | 8/1989 | Helfer | 604/247 |
| 4,892,518 | 1/1990 | Cupp et al. | 604/247 |
| 4,973,319 | 11/1990 | Melsky | 604/247 |
| 5,030,210 | 7/1991 | Alchas | 604/247 |
| 5,092,855 | 3/1992 | Pardes | 604/247 |
| 5,112,301 | 5/1992 | Fenton, Jr. et al. | 604/247 |
| 5,147,332 | 9/1992 | Moorehead | 604/247 |

FOREIGN PATENT DOCUMENTS

| | | |
|---|---|---|
| 336530 | 5/1921 | Fed. Rep. of Germany. |
| 2233293 | 1/1973 | Fed. Rep. of Germany ........ 600/16 |

OTHER PUBLICATIONS

Two-page brochure entitled "Cath-tech ™ CV Catheter", Catheter Technology Corporation, Salt Lake City, Utah (Exhibit A).

Four-page brochure entitled "LifePort®, Vascular Access System", Strato Medical Corporation, Beverly, Massachusetts, Apr., 1987 (Exhibit B).

"Infusaid® Price List", 5 pages, Dec. 31, 1985 (Exhibit C).

Two-page brochure entitled "Port-A-Cath® Implantable Access System", Pharmacia Deltec Inc., St. Paul, Minnesota, Apr., 1988 (Exhibit D).

Four-page brochure entitled "Q-PORT, Subcutaneous Vascular Access Port", Quinton Instrument Company, Seattle, Washington, May, 1987 (Exhibit E).

Four-page brochure entitled "BURRON introduces.. . IM-PLANTOFIX® Drug Delivery Systems", Burron Medical Inc., Bethlehem, Pennsylvania (Exhibit F).

*Primary Examiner*—Ralph Lewis
*Attorney, Agent, or Firm*—Merchant, Gould, Smith, Edell, Welter & Schmidt

[57] ABSTRACT

A vascular access system (20) utilizing a catheter (22) having at least one lumen with a bidirectional check valve assembly (24).

12 Claims, 4 Drawing Sheets

BIDIRECTIONAL CHECK VALVE CATHETER

This is a continuation of application Ser. No. 07/616,737, filed Nov. 21, 1990, now abandoned, which is a continuation of application Ser. No. 07/305,971, filed Feb. 2, 1989, now abandoned.

BACKGROUND OF THE INVENTION

The present invention relates to a catheter having a bidirectional check valve proximate the tip for controlling fluid flow into and out of the catheter.

There are many medical requirements for chronic vascular access including neonatal umbilical vein cannulation, hyperalimentation, chemotherapy, permanent intravascular site for portable drug infusion devices, hemodialysis, plasmapheresis, and, repeated blood sampling. These procedures are performed by using either transcutaneous or totally implanted intravascular catheters.

Examples of transcutaneous catheters include the Broviak and Hickman central venous catheters (Evermed, Kirkland, Wash.) as well as many similar products generically termed subclavian catheters. Catheters in this category may be generally described as being plastic or rubber tubes with female luer fittings at one end. Catheter patency is maintained by filling the catheter lumen with a solution containing an anticoagulant (heparin) between uses. Since the anticoagulant consistently diffuses from the lumen and into the bloodstream, the catheter has to be refilled at 2-3 day intervals in order to prevent a clot from forming at the distal tip.

The Shiley Vas-Cath (Shiley, Inc., Irvine, Calif.) is a transcutaneous subclavian catheter which differs from subclavian catheters in that it has a removable lining. In the event that the catheter clots, the lining, which contains the clot, is extracted from the outer sheath and replaced.

Another solution to catheter lumen clotting involves the insertion of a solid flexible plastic rod, called an obturator, into the catheter lumen between uses. The obturator completely occupies the catheter lumen and therefore prevents diffusion of blood components and subsequent formation of a clot.

An alternate obturated design is the Wigness/Anderson U.S. Pat. No. 4,705,501 entitled, "Bidirectional Antireflux Vascular Access System", which features a self-contained flexible obturator which resembles a bladder which runs the length of the catheter lumen and is not removed between uses, but is instead shifted between the "active" state (where the lumen is open) and the "dormant" state (where the lumen is occluded by the obturator).

The advantages offered by an intravascular catheter in which the lumen may be closed and therefore isolated from the blood stream when it is not in use are:

1. It is resistant to occlusion from thrombosis;
2. It decreases the risk of air embolism; and
3. It requires less maintenance (e.g., heparinization and irrigation).

Examples of totally implantable catheters, generically referred to as "ports", include the "Infuse-A-Port" (Shiley-Infusaid, Inc., Norwood, Mass.), the "Q-Port" (Quinton Instrument Co., Seattle, Wash.), and the "Port-A-Cath" (Pharmacia-Deltec, Inc., St. Paul, Minn.). Ports are similar to subclavian catheters except that the female luer fitting is replaced by a metal or plastic manifold which houses the fluid conduits between a rubber access septum and the catheter connector. Although the catheters are routinely filled with a heparin solution between uses, if the time interval between catheter uses is relatively long (weeks instead of days), each therapy session is initiated by blowing a small clot into the vasculature.

Advantages offered by a catheter which furthermore is totally implantable are:

1. Longer useful life due to reduced risk of infection;
2. Fewer recannulations and therefore less discomfort to the patient; and
3. More patient freedom (the patient may shower, bathe or swim without having to perform special catheter maintenance).

Designs featuring removable obturators or replaceable linings cannot be modified to be totally implantable by simply attaching them to a port, since that would require that a relatively large, solid element be passed through the skin, subcutaneous tissue and catheter septum with each use.

In order to achieve total implantability of the previously described Wigness/Anderson obturated catheter, it is attached either to a special manifold (Wigness/Dorman patent application dated Oct. 6, 1987, U.S. Ser. No. 105,740, entitled, "Implantable Intravascular Access System") or two septa—one for the functional lumen, and one which is used for shifting the obturator.

Diffusion or aspiration of blood into the subclavian-type catheters may be prevented by adding a check valve to their intravascular tips. The Dorman U.S. Pat. No. 4,657,536 entitled, "Check Valve Catheter" describes a sleeve type one-way check valve design for this purpose. While this design prevents blood components from clotting the tip, it does not allow withdrawal of a blood sample—a maneuver that is sometimes desirable and commonly carried out with subclavian catheters and ports. A commercially available port with a one-way check valve at the tip is the "Implantofix" (Burron Medical Inc., Bethlehem, Pa.).

One commercially available catheter featuring a slit valve at the tip which allows both aspiration of blood and infusion of fluids and yet precludes the diffusion of blood components into the lumen between therapy sessions is the Groshong Catheter (Catheter Technology Corporation, Salt Lake City, Utah). This catheter is available both as a transcutaneous appliance and also as a port.

The present invention solves many problems associated with the prior art.

SUMMARY OF THE INVENTION

The present invention relates to a catheter having a bidirectional check valve.

One embodiment of the present invention is an intravascular catheter featuring inlet and outlet check valve action which is controlled by separate valves. The inlet check valve is a tubular rubber element, located in the catheter lumen, which is normally closed against a fixed geometry inlet orifice. Blood sampling is achieved by aspirating, on a proximal end of the catheter, with enough force to create a pressure drop between the blood stream and the catheter lumen which is sufficient to overcome the elastic forces within the wall of the tubular valve, causing the valve to collapse open, thus permitting blood withdrawal. The outlet check valve is an elastic rubber sleeve which is normally closed against a fixed geometry outlet orifice from the vascular side of the catheter. Fluid infusion into the catheter lumen increases the lumen pressure until it is substantially higher than the elastic forces within the valve sleeve plus intravascular blood pressure, at that point fluid is injected via the outlet port through a variable annular passageway created between the sleeve and the vascular side of the catheter.

In an alternative embodiment the two check valve functions are performed by a single valve element. In this embodiment the wall of the tubular rubber element is reinforced by winding a flexible, nonelastic material about the tubular element along its entire length. Properly embedded in the wall of the tubular element, the reinforcement material allows the tubular element to collapse open and perform as an inlet check valve; however, the reinforcement material does not permit significant expansion of the tubular rubber element. The catheter wall in this embodiment is reasonably elastic proximate the fixed geometry inlet orifice which now also serves as an outlet orifice. An increase in fluid pressure in the lumen of the catheter will cause the catheter wall to expand beyond the diameter of the tubular rubber element until a passageway is created between the tubular rubber element and the catheter wall thereby enabling fluid to be expelled through a variable annular orifice created between the tubular rubber element and the wall of the catheter and subsequently out via the fixed geometry port.

A particular advantage of one embodiment of the present invention is that it provides an intravascular catheter design which permits long-term placement in the blood stream without requiring routine anticoagulant flushing in order to prevent thrombus formation within the catheter lumen. This is achieved by controlling communication between the catheter lumen and the bloodstream with normally closed check valves.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, wherein like reference numerals indicate corresponding parts throughout the several views.

DETAILED DESCRIPTION OF THE PREFERRED EMBODIMENT

Figure 1A:
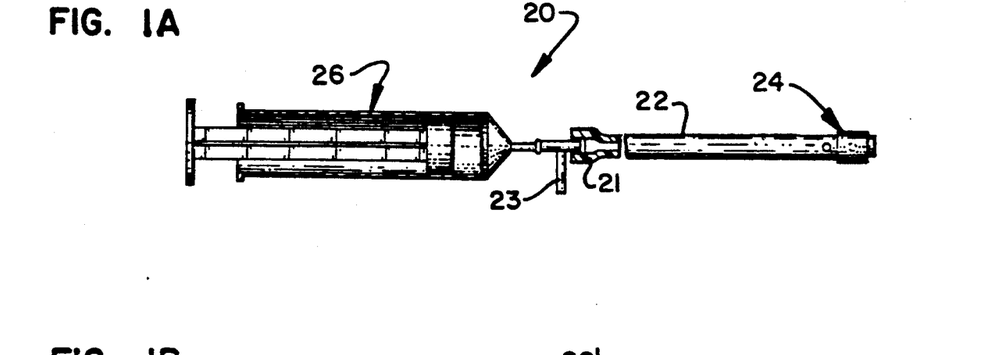
FIG. 1A is a diagrammatic view of a vascular access system utilizing a catheter having a bidirectional check valve utilizing a syringe-stopcock subassembly, as typically used on transcutaneously placed catheters, in accordance with the principles of the present invention.
Figure 1B:
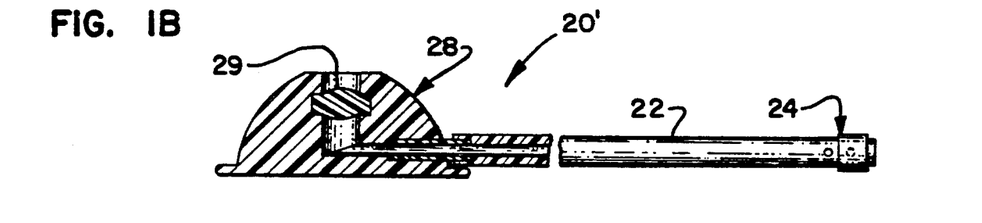
FIG. 1B is a view similar to FIG. 1A illustrating a vascular access system wherein the syringe-stopcock assembly is replaced by an implantable manifold subassembly.

Referring now to the drawings there is shown in FIG. 1A a vascular access system 20 utilizing a single lumen catheter 22 having a bidirectional check valve assembly 24 in accordance with the principles of the present invention. The vascular access system 20 shown in FIG. 1 typically uses transcutaneously placed catheters. Fluid injection and aspiration is shown being accomplished by the use of a syringe-stopcock subassembly 26 which is suitably connected to the exposed end of the catheter 22. FIG. 1B illustrates a vascular access system 20 which incorporates an implantable manifold subassembly 28 such that the vascular access system 20' is totally implantable in the body. The manifold subassembly 28 includes a self-sealing septum 29 through which a needle can be inserted to inject fluid into the manifold subassembly 28. The bidirectional check valve catheter of the present invention can be used with either of the vascular access systems shown in FIGS. 1A,B.

Figure 2:
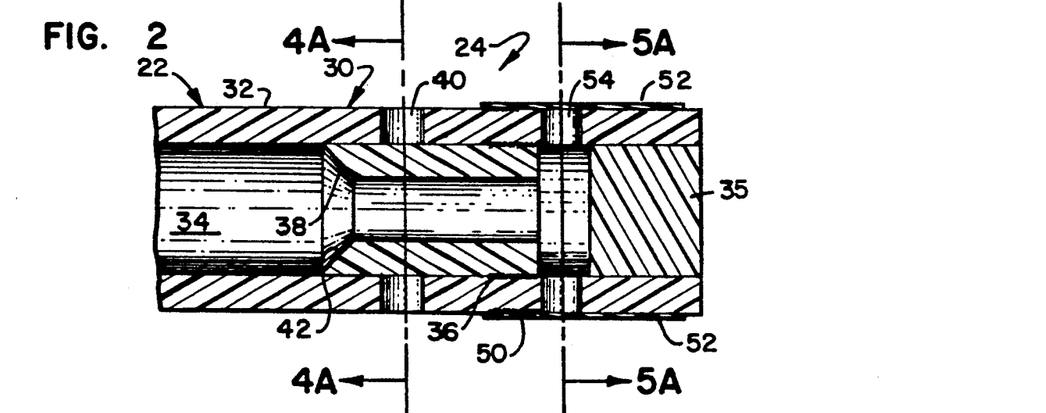
FIG. 2 is a cross-sectional view of a catheter tip portion incorporating an embodiment of a bidirectional check valve assembly in accordance with the principles of the present invention.
Figure 3A:
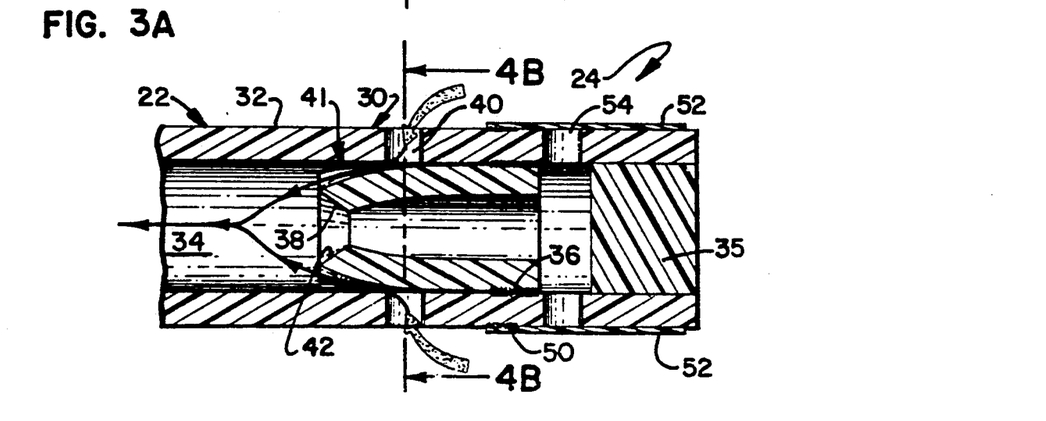
FIG. 3A is a view similar to FIG. 2 illustrating the inlet check valve in an open state such as when aspirating blood into the lumen of the catheter.
Figure 4A:
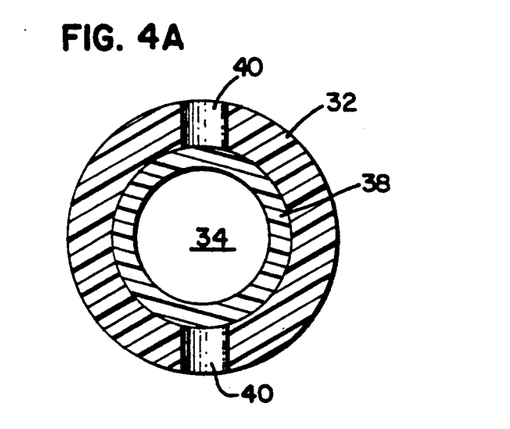
FIG. 4A is a cross-sectional view taken generally along line 4A in FIG. 2 illustrating the inlet check valve in its normally closed state.
Figure 4B:
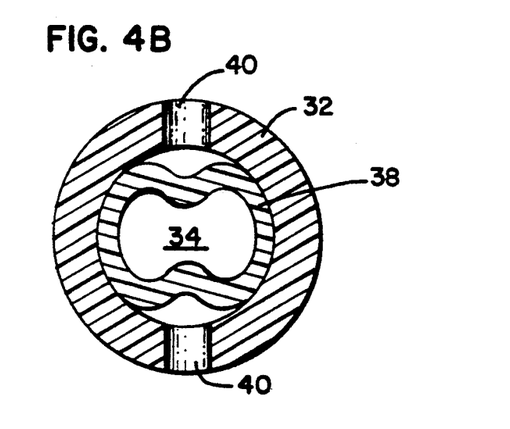
FIG. 4B is a cross-sectional view taken generally along line 4B of FIG. 3A illustrating the inlet check valve in its opened state.

Referring now to FIG. 2, there is illustrated a preferred embodiment of a bidirectional check valve assembly 24 in accordance with the principles of the present invention. A distal tip portion 30 of the catheter 22 is illustrated. The catheter 22 includes a hollow tubular wall member 32 defining a central lumen 34. The distal end of the catheter 22 is closed by a plug member 35. Bonded at location 36 to an inner surface of the central lumen 34 is a hollow tubular member 38 which is also referred to herein as an inlet check valve. The tubular member 38 covers two fixed geometry, diametrically opposed inlet ports 40 in the tubular wall 32 of the catheter 22. A proximal end 42 of the tubular member 38 is tapered as illustrated. In its normal state, the tubular member 38 covers the inlet ports 40 to form a substantially fluid-tight seal so as to prevent body fluid from entering into the catheter 22. However, when a syringe or other device is used to create a decrease in fluid pressure inside the central lumen 34, the tubular member 38 partially collapses to open the inlet ports 40 and allows fluid to flow from the body and into the lumen 34 as generally illustrated in FIG. 3A. FIGS. 4A,B respectively illustrate the tubular member 38 in its normal state and when it is partially collapsed due to a decrease in fluid pressure in the lumen 34 such as when aspirating fluids from the body. As illustrated in FIG. 4B, when the tubular member 38 partially collapses, it forms passageways 41 from the lumen 34 to the inlet ports 40.

Figure 3B:
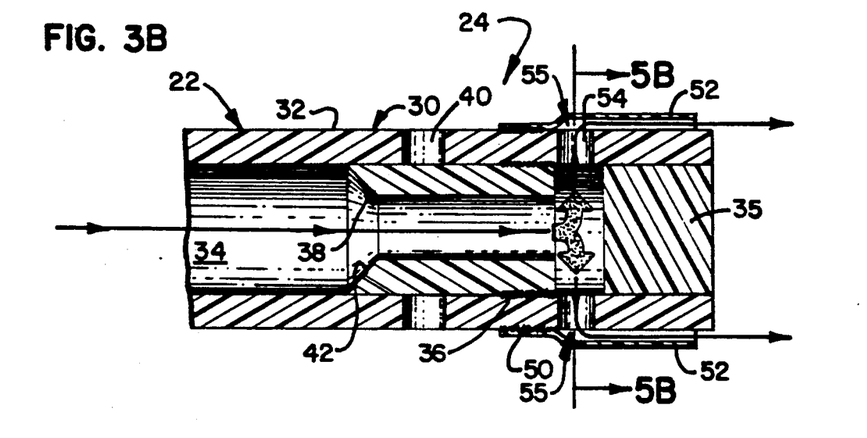
FIG. 3B is a view similar to FIG. 2 illustrating the outlet check valve in an open state such as when injecting fluid from the catheter lumen into the body.
Figure 5A:
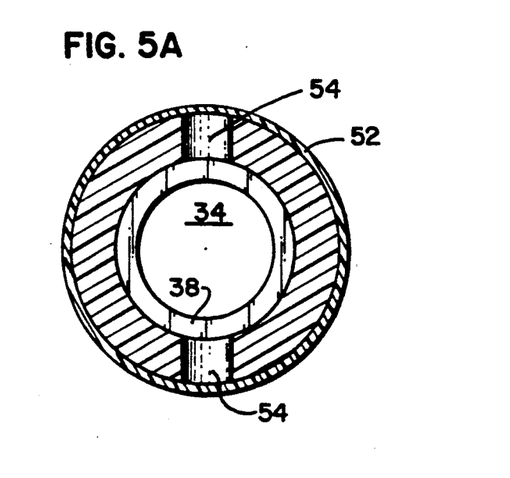
FIG. 5A is a cross-sectional view taken generally along 5A of FIG. 2 illustrating the outlet check valve in its normally closed state.
Figure 5B:
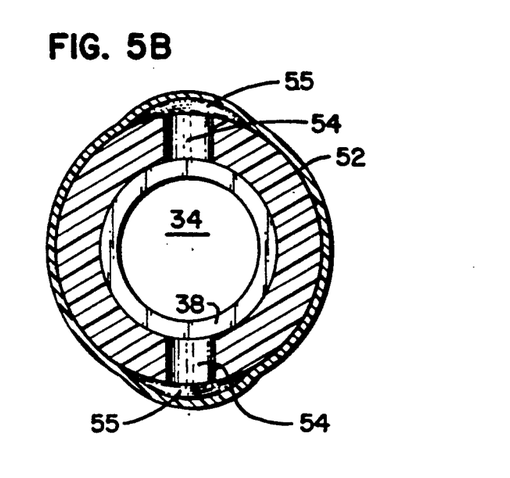
FIG. 5B is a cross-sectional view taken generally along 5B of FIG. 3B illustrating the outlet check valve in its opened state.

As further illustrated in FIG. 2, bonded at 50 to an exterior surface of the catheter wall member 32, is an elastic sleeve 52 which is also referred to herein as an exit check valve. It will be appreciated that the sleeve might be made out of silicone rubber or any number of suitable materials. The elastic sleeve 52 covers two fixed geometry, diametrically opposed exit ports 54 in the tubular wall 32 of the catheter 22. The exit ports 54 are axially removed from the inlet ports 40 toward the distal end of the catheter 22. In one embodiment, in its normal state, the elastic sleeve 52 covers the exit ports 54 to form a substantially fluid-tight seal so as to prevent body fluid from entering the lumen 34 of the catheter. When a syringe or other device is used to create an increase in pressure inside the central lumen 34, the elastic sheath 52 partially expands to open the exit ports 54 and allows fluid to flow from the lumen 34 into the body as generally illustrated in FIG. 3B. FIGS. 5A,B illustrate the elastic sheath 52 in its normal state and when it is partially expanded due to an increase in fluid pressure in the lumen 34 such as when injecting fluids into the body. In yet other embodiments, wherein fluid is continuously being delivered to the body, the elastic sleeve 52 might remain partially expanded. As illustrated in FIG. 5B, when the elastic sleeve 52 is partially expanded, it forms passageways 55 from the lumen 34 and the exit ports 54 into the body 55.

Figure 6:
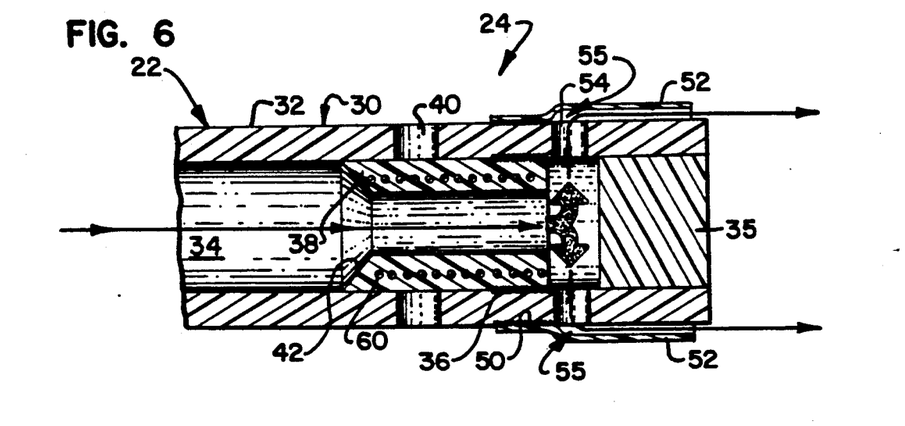
FIG. 6 is a view similar to FIG. 2 illustrating an alternative embodiment of the exit valve tubular member including reinforcement material.

Illustrated in FIG. 6 is an alternate embodiment of the present invention wherein the tubular member 38 is reinforced by a flexible, nonelastic material or fabric 60 embedded in the tubular member 38 and wound in a coil along the length of the tubular member 38. The nonelastic material might be made of any number of materials such as polyurethane, etc. The reinforcement material 60 allows the tubular member 38 to collapse open and perform as an inlet check valve as generally discussed above; however, the reinforcement material 60 does not permit significant expansion of the tubular member 38. It will be appreciated, that in alternate embodiments, the tubular member 38 might be made of a nonelastic flexible sleeve or be constructed as a mesh or any number of other ways.

Figure 7A:
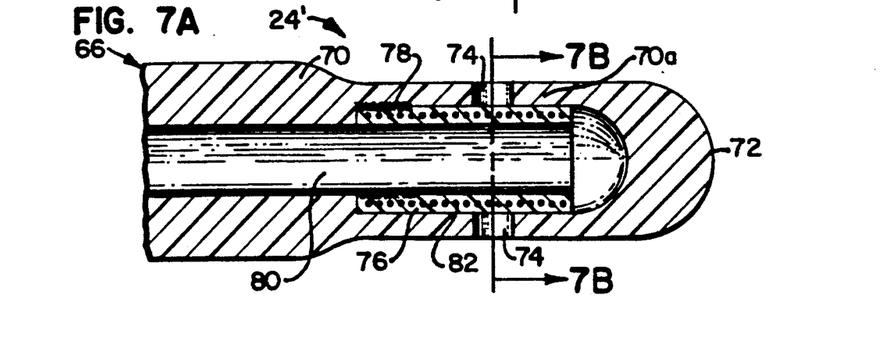
FIG. 7A is a cross-sectional view of a catheter tip portion illustrating an alternate embodiment of a bidirectional check valve assembly in accordance with the principles of the present invention.
Figure 7B:
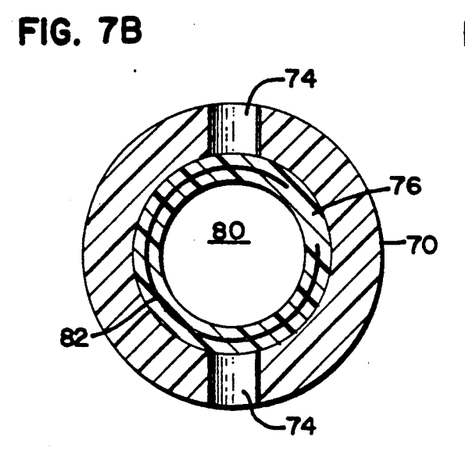
FIG. 7B is a cross-sectional view taken generally along line 7B of FIG. 7A illustrating the bidirectional check valve in its normally closed state.
Figure 7C:
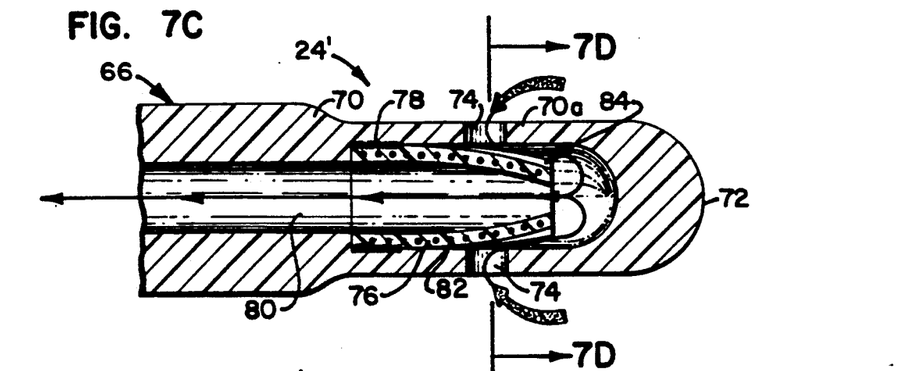
FIG. 7C is a cross-sectional view similar to that of FIG. 7A illustrating the bidirectional check valve assembly in its fluid inlet state.
Figure 7D:
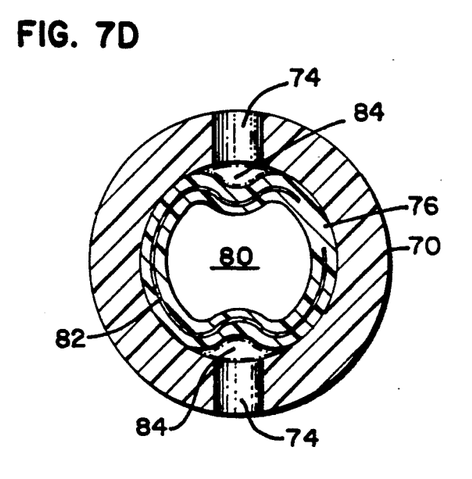
FIG. 7D is a cross-sectional view as seen generally along line 7D of FIG. 7C.

Illustrated in FIGS. 7A-F, is yet another embodiment of a bidirectional check valve assembly 24'. In this embodiment, a catheter 66 is shown as including a tubular wall member 70 which is thinner along an elastic portion 70a close to its distal end 72. The distal end 72 is shown as being of one piece with the wall member 70 and is much thicker than the wall portion 70a. Two diametrically opposed ports 74 are defined in the wall portion 70a. A tubular member 76 is bonded at location 78 to an interior wall of a lumen 80 of the catheter 66. The tubular member 76 includes embedded therein coiled reinforcement material 82 as discussed previously. In its normal state, as generally illustrated in FIGS. 7A,B, the tubular member 76 covers the ports 74 to form a substantially fluid-tight seal so as to prevent fluid from exiting or entering the lumen 80 to and from the body. When a syringe or other device is used to create a reduction in pressure in the lumen 80, the tubular member 76 partially collapses to open the ports 74 and allows fluid to flow from the body and into the lumen as generally illustrated in FIGS. 7C,D. When the tubular member 76 partially collapses it forms passageways 84 extending from the lumen 80 to the ports 74.

Figure 7E:
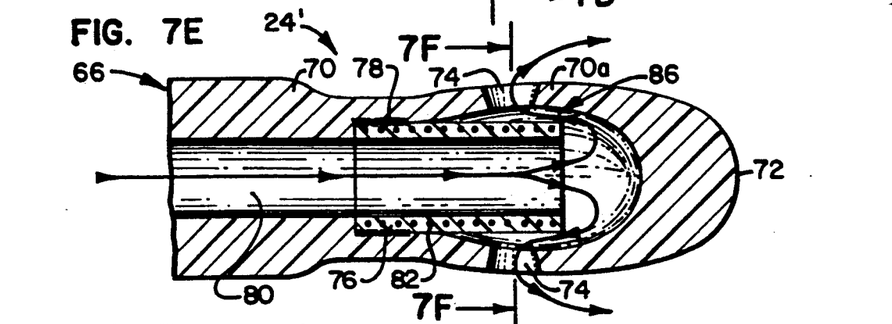
FIG. 7E is a cross-sectional view similar to FIG. 7A illustrating the bidirectional check valve in its fluid exit state.
Figure 7F:
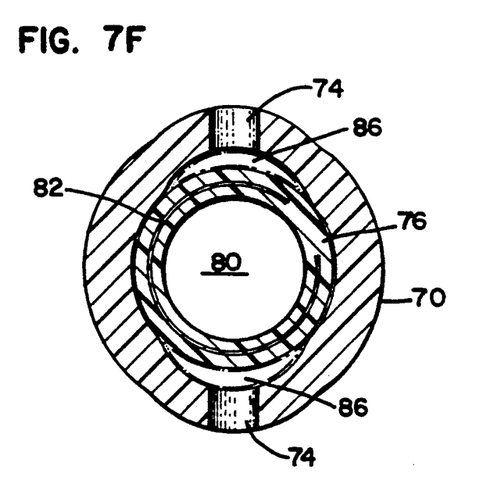
FIG. 7F is a cross-sectional view as seen generally along line 7F of FIG. 7E.

When a syringe or other device is used to create an increase in pressure in the lumen 80, the catheter wall portion 70a expands to open the ports 74 and allows fluid to flow from the lumen 80 and into the body as generally illustrated in FIGS. 7E,F. When the wall portion 70a expands, it forms passageways 86 extending from the lumen 80 to the ports 74.

Operation of vascular access systems incorporating catheters with bidirectional check valve assemblies in accordance with the principles of the present invention will now be described. With respect to the first embodiment shown in FIG. 2, when the catheter 22 is not in use, the valves of the bidirectional check valve assembly 24 are in their normally closed state as generally illustrated in FIG. 2. There is no fluid communication between the bloodstream and the catheter lumen 34 and a female luer fitting 21 at a proximal end of a percutaneously placed catheter is occluded by a stopcock 23. It will be appreciated that the proximal end of the catheter 22 might be occluded by any number of methods other than a stopcock such as a punctureable septum or a solid plug. Aspiration of a blood sample is achieved by installing an empty syringe 26 on the female luer fitting 21. Withdrawal of the syringe barrel causes a decrease in pressure within the catheter lumen 34. When the pressure drop from the blood vessel to the catheter lumen exceeds the elastic forces within the wall of the tubular compression valve member 38, the valve 38 is forced open and blood is aspirated via the fixed geometry inlet port 40 and the variable annular inlet passageway 41 into the catheter lumen 34 and onto the syringe 26 via the catheter 22. At the end of a blood withdrawal procedure, the catheter 22 is normally flushed with a normal saline solution (0.9% NaCl) by replacing the blood collecting syringe 26 with a syringe 26 containing normal saline and injecting the contents into the catheter. This first creates a pressure increase within the catheter lumen 34 until the difference between the lumen pressure and the vascular blood pressure exceeds the elastic forces within the exit port check valve sleeve 52, at which time, normal saline is forced via the fixed geometry exit port 54 through the variable annular exit passageway 55 into the bloodstream. In this manner, sufficient normal saline volume is infused in order to totally rinse the lumen 34 of any blood components.

It will be appreciated that the sequence of events for the totally implantable vascular access system as shown in FIG. 1B is similar to the percutaneous vascular access system design shown in FIG. 1A except that instead of connecting a syringe 26 directly to the female luer fitting 21 of the catheter 22, the syringe 26 is connected to a hypodermic needle which is in turn inserted through the skin and the access septum of the manifold 28 and into the manifold's plenum which in turn communicates with the catheter lumen 34.

The operation of the alternative embodiment generally illustrated in FIGS. 7A-7F, in which the valveing functions are combined into a single element, will now be described. Aspiration by the syringe 26 causes a pressure drop in the lumen 80. When the lumen pressure drops below the blood pressure by an amount significantly greater than the elastic forces in the wall of the nonexpandable tubular valve member 76, the valve opens and blood is drawn first into the fixed geometry port 74 and then into the lumen 80 of the catheter via the variable passageway 84 between the tubular valve member 76 and an internal wall of the catheter 66. Fluid injection and/or flushing by use of the syringe 26 causes an increase in the fluid pressure within the catheter lumen 80 until it exceeds blood pressure by an amount significantly greater than the elastic forces in the relatively elastic portion 70a of the catheter wall 70 which contains the fixed geometry port 74 and encompasses the nonexpandable tubular valve member 76. Since the girth of the nonexpandable tubular valve member 76 cannot increase significantly due to the presence of the reinforcement material 82, expansion of the relatively elastic portion 70a of the catheter wall 70 is accompanied by an enlargement of the annular passageway 84. When the annular passageway 84 opens, fluid is injected into the bloodstream via the fixed geometry port 74.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A bidirectional check valve catheter tip for intravascular placement in a living body, comprising:
    (a) an elongated bio-compatible, tubular member having a distal end and a proximal end;
    (b) at least one lumen being defined by the tubular member, first port means for transferring fluid into the lumen, and second port means for transferring fluid from the lumen, the first port means being located proximally of the second port means; and
    (c) first check valve means for controlling fluid flow through the first port means and second check valve means for controlling fluid flow through the second port means, the first check valve means normally closing the first port means and being responsive to changes in fluid pressure for allowing fluid to flow into the lumen through the first port means upon establishment of a negative pressure differential having a magnitude greater than a first value and being defined by the pressure in a region of the lumen adjacent to the first port means being low relative to the pressure in a region exterior to the lumen adjacent to the first port means, and the second check valve means normally closing the second port means so there is substantially no cavity formed in the catheter tip on a distal side of where the second check valve means normally closes the second port means, the second check valve means being responsive to changes in fluid pressure for allowing fluid to flow from the lumen through the second port means upon establishment of a positive pressure differential having a magnitude greater than a second value and being defined by the pressure in a region of the lumen adjacent to the second port means being high relative to the pressure in a region exterior to the lumen adjacent to the second port means.

2. A catheter tip in accordance with claim 1, wherein the first and second port means includes at least a first port longitudinally spaced apart from at least a second port, the first check valve means includes tubular compression means being attached to an interior of the tubular member and normally closing the first port for allowing fluid to flow into the lumen upon detection of decreased pressure such as when aspirating blood from the body into the lumen, the second check valve means includes elastic sleeve means being attached to an exterior of the tubular member and normally closing the second port for allowing fluid to flow from the lumen upon detection of increased pressure such as when injecting drugs from the lumen to the body.

3. A catheter tip in accordance with claim 2, wherein the tubular compression means includes a reinforcement material embedded therein.

4. A bidirectional check valve catheter tip for intravascular placement in a living body, comprising:
    (a) an elongated bio-compatible, tubular member having a distal end and a proximal end;
    (b) at least one lumen being defined by the tubular member, the lumen being open proximate the proximal end and closed proximate the distal end, at least one port being defined in a wall of the tubular member encircling the lumen for transferring fluid from the lumen; and
    (c) first and second check valve means for controlling fluid flow through the port, wherein the first check valve means includes tubular compression means attached to an interior of the tubular member and normally closing the port and being responsive to changes in fluid pressure for allowing fluid to flow into the lumen upon establishment of a negative pressure differential having a magnitude greater than a first value and being defined by the pressure in a region of the lumen adjacent to the port being low relative to the pressure in a region exterior to the lumen adjacent to the port, and further wherein the second check valve means includes the distal end portion of the tubular member, the distal end portion being elastic proximate the port whereby upon establishment of a positive pressure differential having a magnitude greater than a second value and being defined by the pressure in a region of the lumen adjacent to the port being high relative to the pressure in a region exterior to the lumen adjacent to the port, the distal end portion expands opening the port and allowing fluid to flow from the lumen to the body.

5. A catheter tip in accordance with claim 4, wherein the tubular compression means includes a reinforcement material embedded therein.

6. A catheter for intravascular placement in a living body, comprising:
    (a) an elongated bio-compatible, flexible tubular member having a distal end and a proximal end adapted for interconnection to a fluid injection/aspiration device;
    (b) at least one lumen being defined by the tubular member, first port means for transferring fluid to the lumen from the body, and second port means for transferring fluid from the lumen to the body, the first port means being located proximally of the second port means; and (c) first check valve means for controlling fluid flow through the first port means and second check valve means for controlling fluid flow through the second port means, the first check valve means normally closing the first port means and being responsive to changes in fluid pressure for allowing fluid to flow into the lumen upon establishment of a negative pressure differential having a magnitude greater than a first predetermined value and being defined by the pressure in a region of the lumen adjacent to the first port means being low relative to the pressure in a region of the body exterior to the catheter adjacent to the first port means, the second check valve means normally closing the second port means so there is substantially no cavity formed in the catheter on a distal side of where the second check valve means normally closes the second port means, the second check valve means being responsive to changes in fluid pressure for allowing fluid to flow from the lumen to the body upon establishment of a positive pressure differential having a magnitude greater than a second predetermined value and being defined by the pressure in a region of the lumen adjacent to the second port means being high relative to the pressure in a region of a body exterior to said catheter adjacent to the second port means.

7. A vascular access system for intravascular placement in a living body, comprising:

(a) an elongated bio-compatible, flexible tubular member having a distal end and a proximal end;

(b) at least one lumen being defined by the tubular member, first port means for transferring fluid to the lumen from the body in a direction toward the proximal end, and second port means being defined in a wall of the tubular member for transferring fluid from the lumen to the body in a direction away from the proximal end, the first port means being located proximally of the second port means;

(c) fluid aspiration/injection means interconnected to the proximal end of the tubular member and in fluid communication with the lumen for aspirating fluid from and injecting fluid into the lumen; and (d) first check valve means for controlling fluid flow through the first port means and second check valve means for controlling fluid flow through the second port means, the first check valve means normally closing the first port means and being responsive to changes in fluid pressure for allowing fluid to flow into the lumen upon establishment of a negative pressure differential having a magnitude greater than a first predetermined value and being defined by the pressure in the region of the lumen adjacent to the first port means being low relative to the pressure in the region of the body exterior to the lumen adjacent to the first port means, the second check valve means normally closing the second port means so there is substantially no cavity formed in the tubular member on a distal side of where the second check valve means normally closes the second port means, the second check valve means being responsive to changes in fluid pressure for allowing fluid to flow from the lumen upon establishment of a positive pressure differential having a magnitude greater than a second predetermined value and being defined by the pressure in the region of the lumen adjacent to the second port means being high relative to the pressure in the region of the body exterior to said catheter adjacent to the second port means.

8. A bidirectional check valve catheter tip for intravascular placement in a living body, comprising:

(a) an elongated bio-compatible, flexible tubular member having a distal end and a proximal end;

(b) at least one lumen being defined by the tubular member, the lumen being open proximate the proximal end and closed proximate the distal end, port means being defined in a wall of the tubular member encircling the lumen for transferring fluid between the lumen and the body;

(c) check valve means for controlling fluid flow through the port means between the lumen and the body, the check valve means normally closing the port means and being responsive to fluid pressure for allowing fluid flow into the lumen upon establishment of a negative pressure differential having a magnitude greater then a first predetermined value and being defined by the pressure in a region of the lumen adjacent to the port means being low relative to the pressure in a region of the body exterior to the catheter adjacent to the port means, the check valve means being further responsive to changes in fluid pressure for allowing fluid to flow form the lumen to the body upon establishment of a positive pressure differential having a magnitude greater than a second predetermined value and being defined by the pressure in a region of the lumen adjacent to the port means being high relative to the pressure in a region of the body exterior to the catheter adjacent to the port means; and (d) wherein the check valve means includes tubular compression means attached to an interior of the tubular member and normally closing the port means for allowing fluid to flow into the lumen upon occurrence of the negative pressure differential, the distal end portion of the tubular member being elastic proximate the port means, whereby upon establishment of the positive pressure differential, the distal end portion expands opening the orifice means and allowing fluid to flow from the lumen to the body.

9. A catheter tip in accordance with claim 8, wherein the tubular compression means includes a reinforcement material embedded therein.

10. A bidirectional check valve catheter tip, comprising:

(a) an elongated member having a distal end and a proximal end;

(b) at least one lumen being defined by the tubular member, the lumen including a port in a wall of the lumen for transferring fluid to and from the lumen; and (c) first unidirectional check valve means responsive to changes in fluid pressure for allowing fluid flow into the lumen through the port and separate and distinct second unidirectional check valve means responsive to changes in fluid pressure for allowing fluid flow from the lumen through the port.

11. A bidirectional check valve catheter tip, comprising:

(a) an elongated member having a distal end and a proximal end;

(b) at least one lumen being defined by the elongated member, the lumen including inlet port means for transferring fluid into the lumen and outlet port means for transferring fluid from the lumen, the inlet port means being located proximally of the outlet port means; and (c) first unidirectional check valve means responsive to changes in fluid pressure for allowing fluid flow into the lumen through the inlet port means and second unidirectional check valve means responsive to changes in fluid pressure for allowing fluid flow from the lumen through the outlet port means, the second check valve means closing the outlet port means so that there is substantially no cavity in the catheter tip on a distal side of where the second unidirectional check valve means normally closes the outlet port means.

12. A bidirectional check valve catheter tip, comprising:

(a) an elongated tubular member having a distal end and a proximal end, said tubular member being closed at said distal end;

(b) at least one lumen being defined by and extending along the tubular member, the lumen including inlet port means for transferring fluid into the lumen and outlet port means for transferring fluid from the lumen, the outlet port means being located distally of the inlet port means; and (c) first unidirectional check valve means responsive to changes in fluid pressure for allowing fluid flow into the lumen through the inlet port means and second unidirectional check valve means responsive to changes in fluid pressure for allowing fluid flow from the lumen through the outlet port means, the second check valve means including means for closing the outlet port means proximate the distal end whereby there is substantially no cavity in the catheter tip on a distal side of where the second unidirectional check valve means normally closes the outlet port means.

* * * * *